United States Patent [19]

Aoyama et al.

[11] 4,208,917
[45] Jun. 24, 1980

[54] DEVICE FOR INSPECTING SPOT WELDS

[75] Inventors: Shigetsune Aoyama, Okazaki; Kiyokazu Asai, Nagoya, both of Japan

[73] Assignee: Kabushiki Kaisha Toyota Chuo Kenkyusho, Aichi, Japan

[21] Appl. No.: 15,760

[22] Filed: Feb. 27, 1979

[30] Foreign Application Priority Data

Feb. 27, 1978 [JP] Japan ................................. 53-22444

[51] Int. Cl.² ............................................. G01N 29/00
[52] U.S. Cl. ......................................... 73/644; 73/588
[58] Field of Search ................. 73/644, 588, 627, 629, 73/632, 630, 631, 596, 598

[56] References Cited
U.S. PATENT DOCUMENTS 4,099,045 7/1978 Okuda et al. ...................... 73/629 X

FOREIGN PATENT DOCUMENTS 50-798206 of 1975 Japan .

Primary Examiner—Jerry W. Myracle
Attorney, Agent, or Firm—Oblon, Fisher, Spivak, McClelland & Maier

[57] ABSTRACT

A device for inspecting spot welds which comprises a probe for receiving a reflected wave from an inspection material, a weld state display unit for displaying a waveform, a pulse interval and a number of pulses of the reflected wave, and a wave guide connected to an end portion of the probe, for guiding the reflected wave from the inspection material to the probe. The wave guide has an ultrasonic wave propagating section in the form of a cylinder and an internal ultrasonic wave absorbing section obtained by filling an inside hole of the cylinder with an ultrasonic wave absorbing material, the ultrasonic wave propagating section being so dimensioned that the length of an ultrasonic wave propagating path is within the range calculated from the following equation:

$$L = n\lambda \pm 0.2\lambda$$

where n is an integer value, $\lambda$ is the wavelength (mm) of an ultrasonic wave, and L is the length (mm) of the ultrasonic wave propagating path.

7 Claims, 17 Drawing Figures

DEVICE FOR INSPECTING SPOT WELDS

BACKGROUND OF THE INVENTION

1. Field of the Invention

This invention relates to a spot weld inspecting device for inspecting the size of a nugget in a spot weld by the use of an ultrasonic wave.

2. Description of the Prior Art

Acceptability of a spot weld depends greatly on whether or not the nugget is formed as predetermined. In the case of a good weld, the size of the nugget is slightly larger than or close to the diameter of an electrode tip used in the welding. In the case of a poor weld, the size of the nugget is much smaller than the diameter of the electrode tip, and the weld includes portions not welded. In order to inspect whether or not the nugget is formed to a size which is required for sufficient strength, a spot weld inspecting device using an ultrasonic wave is employed.

A conventional spot weld inspecting device, as shown in FIG. 1 comprises a probe 1, and a display unit 2 such as an oscilloscope. The probe 1 is disposed in contact with a material 3 to be inspected in which plates 31 and 32 are welded together. The probe transmits an ultrasonic wave thereto and receives a wave reflected therefrom. The display unit 2 operates to receive an electrical signal from the probe 1 and to thereby display the reflected wave 21.

However, the conventional probe 1 emits the ultrasonic wave with the entire end face 11 thereof (having substantially the same diameter as that of the welding tip) in contact with the inspection material. Therefore, in the case of a small nugget 4, both the information (reflected wave) from a portion where the nugget 4 is formed and the information from a portion not welded are unseparated when they are received by the probe 1. Accordingly, it has been difficult to determine whether or not the size of the nugget is as large as, or is larger than, the value predetermined to obtain sufficient strength.

In the conventional device, the probe 1 emits an ultrasonic wave pulse in the direction of the inspection material which has been spot-welded through one plate 31 thereof and receives the reflected wave from the inspection material. In the case where the size of the nugget 4 is smaller than the end face 11 of the probe, the portion of the incident wave in the area where the nugget has been formed, passes through the nugget and produces multiple reflection waves 51 between the outer surface of the other plate 32 and the acoustic wave incident surface of the plate 31, while in the area where the nugget has not been formed, multiple reflection waves 52 are produced between the surface of the plate 31, which confronts the plate 32, and the incident surface. These reflected waves 51 and 52 are received by the probe 1 and are displayed on the oscilloscope. Therefore, the reflected waves 52 produced in the portion welded unsatisfactorily appear between the pulses of the reflected waves 51 produced in the portion where the nugget has been formed and welding has been satisfactorily done.

In this case, in order to determine the size of the nugget from the reflected waves 51 and 52, it is necessary to measure the height of the reflected waves 52 in the unsatisfactorily welded portion (the strength of the reflected waves) and to utilize the analytical curve obtained from the relationships between reflected wave height and nugget diameter. However, this method is rather intricate and is low in accuracy.

Thus, the conventional device is disadvantageous in that it cannot be readily utilized to determine whether the weld is satisfactory or not.

In order to solve these problems, the inventors have developed a spot weld inspecting device in which an ultrasonic wave propagating wave guide is arranged on the tip of a probe (Japanese Patent Application No. 105087/1970, published as Japanese Patent Publication No. 15677/1975 and patented as Japanese Patent No. 798206). The wave guide, as shown in FIG. 17, comprises a cylindrical structure 62A serving as an ultrasonic wave propagating section and an ultrasonic wave absorbing material 63A filling a cavity 64A formed in the cylindrical structure 62A. The cylindrical structure 62A is provided with an annular contact surface 65A at one end which may be brought into contact with the inspection material. In FIG. 17, reference character 61A designates a recess into which the probe 1 is inserted, and reference character 612A designates a probe connecting surface. In the wave guide, the outside diameter of the contact surface 65A is substantially equal to the outside diameter of an electrode tip for welding and the inside diameter thereof corresponds to the size of a nugget of the minimum size required for welding.

As the wave guide is thus constructed, the information on the central portion of a weld is not received by the probe 1 but the information on the peripheral portion thereof is received by the probe. Therefore, the problems accompanying the above-described conventional device can be solved. More specifically, in inspection, when the size of a nugget is smaller than the size required for welding, the size of the nugget is smaller than the inside diameter of the annular contact surface 65A of the wave guide 6A, and therefore only the information on the not-welded portion is supplied to the wave guide. This information (multiple reflection) is supplied through the probe 1 to the display unit 2, whereby the poor weld can be easily determined. On the other hand, when the size of a nugget is larger than the minimum size required for welding, the size of the nugget is also larger than the inside diameter of the annular contact surface 65A, and therefore the information (multiple reflection) on the welded portion is also supplied to the wave guide 6A, whereby the good weld is determined by a method similar to that in the above-described case.

Thus, the difficulties accompanying the conventional device are eliminated by the provision of a device using the wave guide earlier developed by the inventors.

However, as the distance between the annular contact surface 65A and the probe connecting surface 612A is relatively long, i.e. about 10 mm, in the wave guide (hereinafter referred to as a conventional wave guide, when applicable) in the device developed by the inventors, the following problem is involved when thin plates 1.4 mm or less in thickness are welded.

In the case where inspection is performed with the conventional wave guide, if a probe capable of emitting a strong ultrasonic wave pulse at a relatively low frequency (lower than 5 MHz) is used, the size of a nugget in a spot weld of a plate whose thickness is more than 1.6 mm can be inspected with high accuracy; however, there is a fear that it would be impossible to inspect a spot weld of plates whose thickness is less than 1.4 mm because the individual pulses of multiple reflection in the spot weld could not be separated from one another.

Therefore, the pulse resolution may be improved by using a probe capable of emitting an ultrasonic wave at a high frequency (higher than 10 MHz) or by using a high resolution probe capable of producing pulses in the form of a shock wave, which are short in pulse width. However, since these probes cannot product strong ultrasonic wave pulses, they cannot receive the multiple reflection waves in spot welds with sufficiently high sensitivity. Thus, these probes cannot be utilized for inspecting spot welds of thin plates as described above.

The strength of the ultrasonic wave pulse incident to a spot weld may be increased by decreasing the length of the ultrasonic wave propagating section in the wave guide. However, if the length of the ultrasonic wave propagating section is merely reduced, after the first ultrasonic pulse emitted by the probe has propagated through the wave guide and entered the weld, a part of the energy of the ultrasonic pulse causes reflections to occur repeatedly in the ultrasonic wave propagating section between the annular contact surface 65A and the internal flat surface 612A of the wave guide to thereby produce second, third, fourth, etc., unwanted reflected waves which enter the weld. Accordingly, each of the number of unwanted incident waves causes multiple reflection waves in the weld, which are superposed on the necessary multiple reflection waves in the weld caused by the first incident pulse. Thus, it is impossible to clearly receive the multiple reflection wave in the spot weld merely by reducing the length of the ultrasonic wave propagating section.

However, this problem is not created in the case where, as in the conventional wave guide, the length of the ultrasonic wave propagating section is relatively long, as 10 mm, because the reflected wave pulses of the above-identified type are damped while passing through the long ultrasonic wave propagating section. However, as was described above, with such a long ultrasonic wave propagating section, it is impossible to inspect the spot weld of thin plates.

SUMMARY OF THE INVENTION

Accordingly, an object of the present invention is to provide a device for inspecting the quality of welding in a spot weld.

Another object of the present invention is to provide a device capable of inspecting the size of a nugget in a spot weld reliably and with high accuracy.

A further object of the present invention is to provide a device capable of inspecting the size of a nugget in a spot weld of thin plates less than 1.4 mm in thickness.

The most specific feature of the invention resides in the fact that the length of the ultrasonic wave propagating path in the wave guide is within a particular range.

According to this invention, a spot weld inspecting device is provided which comprises a probe for receiving a reflected wave from a material to be inspected, a weld state display unit for displaying a waveform, a pulse interval and a number of pulses of the reflected wave, and a wave guide connected to an end portion of the probe for guiding the reflected wave from the material to be inspected to the probe. The wave guide has an ultrasonic wave propagating section in the form of a cylinder and an internal ultrasonic wave absorbing section obtained by filling an inside hole of the cylinder with an ultrasonic wave absorbing material. The ultrasonic wave propagating section is so dimensioned that the length of an ultrasonic wave propagating path is within the range calculated from the following equation:

$$L = n\lambda \pm 0.2\lambda$$

where n is an integer value, $\lambda$ is the wavelength (mm) of an ultrasonic wave, and L is the length (mm) of the ultrasonic wave propagating path.

In the wave guide constructed according to the invention even in the case of welding such thin plates as described above, strong multiple reflection waves from the spot weld to be inspected can be received by the probe. Further, since the ultrasonic waves which enter the weld while repeating multiple reflection in the wave guide enter the weld all in the same phase, they can be reflected from the weld back into the wave guide as multiple reflection waves without irregular waveforms. Therefore, the multiple reflection waves of the weld can be clearly displayed on the welding state display unit.

In this invention, a number of multiple reflection waves occur in the wave guide. However, these unwanted reflected waves can be damped in an extremely short time because the reduction of the energy due to reflection is added to the absorption of the ultrasonic waves attributed to the material of the wave guide. For this reason, a strong ultrasonic pulse can be applied to the weld, and the multiple reflection waves from the weld can be received more strongly. Not only a single ultrasonic pulse produced by the probe but also a number of ultrasonic pulses caused by repetitive multiple reflection in the wave guide are applied to the weld. However, since all of these pulses enter the weld with phase differences which are integer multiples of one wave length, all of the multiple reflection waves occurring in the weld are in phase with one another and therefore deformation of the waveform is never caused by mutual interference.

Therefore, it is possible to receive the multiple reflection waves from the weld with high sensitivity, and to obtain a clear waveform. Accordingly, the use of a probe producing high frequency pulses, or a probe producing shock wave type high resolution pulses, as described before is permitted, and inspection of spot welds of thin plates, which has been difficult, can be positively achieved with high accuracy.

It goes without saying that the device according to this invention can be applied to not only the inspection of the welds of thin plates as described above but also the inspection of the welds of thick plates.

BRIEF DESCRIPTION OF THE DRAWINGS

Various other objects, features and attendant advantages of the present invention will be more fully appreciated as the same becomes better understood from the following detailed description when considered in connection with the accompanying drawings wherein like reference characters designate like or corresponding parts throughout the several views, and wherein.

DETAILED DESCRIPTION OF THE PREFERRED EMBODIMENTS

Figure 1:
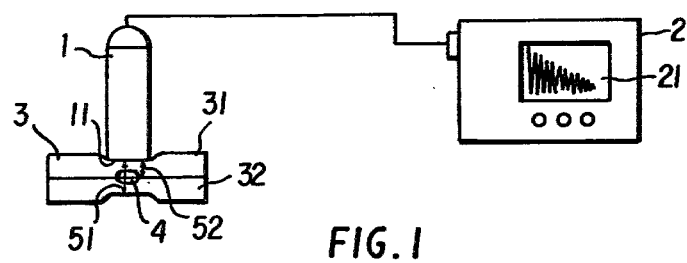
FIG. 1 is an explanatory diagram showing a conventional spot weld inspecting device.

The cylindrical wave guide is designed to guide reflected waves from an inspection material of the present invention to the probe. The wave guide has a probe fixing section at one end and an annular contact surface at the other end, which is brought into contact with the inspection material to allow the ultrasonic wave to enter the inspection material and to receive the reflected waves from the inspection material. The outside diameter of the contact surface is substantially equal to the outside diameter of an electrode tip used in welding, and the inside diameter thereof corresponds to the size of a nugget to be measured.

The inside diameter of one side of the wave guide, which is brought into contact with the end surface of the probe, is not particularly specified, but if it is too large, then the ultrasonic wave propagating area between the guide and the probe is insufficient. The contact surface of the end portion of the wave guide is annular; however, the configuration of the annular contact surface may be circular or elliptic. That is, it may be selected as desired according to the configuration of a nugget formed in a spot weld.

With reference to the wave guide, the term "ultrasonic wave propagating path length" is intended to mean a length twice as long as the length, in an axial direction, between the probe connecting surface which is brought into contact with the end face of the probe and the annular contact surface which is brought into contact with an inspection material.

The most important aspect of this invention is that, as described before, the ultrasonic wave propagating path length L (mm) is within a range calculated from the following equation:

$$L = n\lambda \pm 0.2\lambda$$

where n is an integer value, and $\lambda$ is the wavelength (mm) of an ultrasonic wave used in inspection.

That is, in the ultrasonic wave propagating path length L, a length obtained by multiplying the wavelength of an ultrasonic wave by an integer number is employed as a reference length which can be tolerated within a range of $\pm 0.2\lambda$. The wavelength is determined from the acoustic velocity (m/sec) in the cylindrical structure of the wave guide and the frequency (cycle) of an ultrasonic wave used in inspection. Since the ultrasonic wave propagating path length L is twice as long as the distance between the probe connection surface, and the contact surface, of the cylindrical structure, the distance between the probe connection surface and the contact surface is so designed to be a half ($\frac{1}{2}$) of the length L calculated from the aforementioned equation.

It is preferable that the integer value n is within a range of from 5 to 20 in view of the strength of the wave guide.

In the case where, for instance, the material of the wave guide defines the acoustical velocity in the cylindrical structure to be 3000 m/sec and the frequency of an ultrasonic wave emitted from the end of the probe is 5 MHz ($=5 \times 10^6$ Hz), the wavelength $\lambda$ is 0.6 mm. If, in this case, the value n is eight (8), then the upper limit of the ultrasonic wave propagating path length L is 4.92 mm$=8 \times 0.6 + 0.2 \times 0.6$, and the lower limit thereof is 4.68 mm$=8 \times 0.6 - 0.2 \times 0.6$. Thus, the length L should be within this range.

The ultrasonic wave absorber for absorbing reflected waves in the wave guide is fixedly secured to the whole inner wall of an inside hole formed in the wave guide. The ultrasonic wave absorber may be secured, in the form of a cylinder, to the inner wall; however, the same effect may be obtained by filling the inside hole with an ultrasonic wave absorbing material. The material of the ultrasonic wave absorber may be rubber, paraffin or resin, or mixtures of these materials and tungsten powder or carbon powder.

The probe operates to emit an ultrasonic wave to a material to be inspected, and to receive a reflected wave from the material to be inspected.

In many cases, the welding state display unit is an oscilloscope for observing the waveform of a received signal. However, it may also be a meter indicating the pulse time interval of the received wave, or a meter indicating the number of pulses received whose height is higher than a predetermined value, or a received waveform recorder. Furthermore, it is also possible to electrically measure the echo intervals of multiple reflection waves to digitally display the value thus measured.

Figure 8:
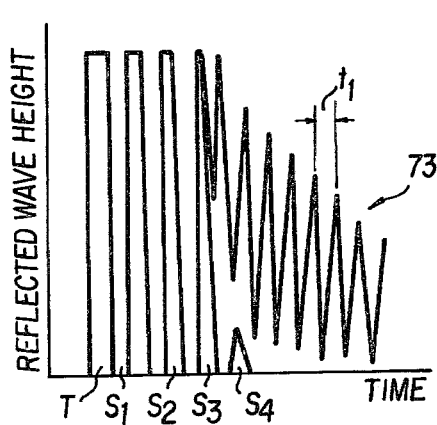
FIGS. 8 and 9 are waveform diagrams showing the relationship between reflected wave height and time in Example 1.

According to the invention, in the case where the probe emits an ultrasonic wave and receives a reflected wave, the ultrasonic wave produced by the probe enters an inspection material annularly through the cylindrical wave guide. When the nugget diameter is substantially equal to or larger than the outside diameter of the contact surface of the wave guide, the ultrasonic wave is passed through the nugget and is then reflected by the outer surface of the inspection material. The wave thus reflected is received through the wave guide by the probe and is then displayed on the oscilloscope or the like. The pulse intervals of the reflected wave in such a case is relatively long as shown in FIG. 8.

Figure 9:
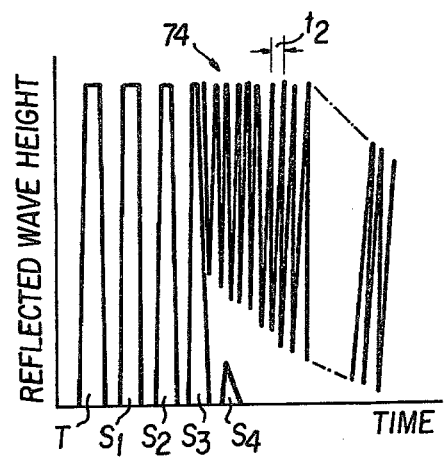

On the other hand, when the nugget diameter is smaller than the inside diameter of the contact surface of the wave guide, the ultrasonic wave entering the inspection material is annularly incident on the peripheral portion outside the nugget; that is, it does not enter the nugget. Therefore, the ultrasonic wave is reflected only in the plate with which the wave guide is in contact. The reflected wave is received through the wave guide by the probe, and the pulse interval thereof is short as shown in FIG. 9. Where the nugget diameter is larger than the inside diameter of the contact surface of the wave guide but smaller than the outside diameter thereof, in the portion where the nugget is formed the incident wave is reflected by the outer surface of the inspection material as was described, and in the portion where no nugget is formed the incident wave is reflected only in the plate with which the wave guide is in contact as was described. Thus, both of the reflected waves are received by the probe, and therefore the waveform thereof is the superposition of the long pulse interval wave and the short pulse interval wave, as described before, thus being irregular.

As the received waveforms are clearly different from one another depending on the relations between the inside diameter of the wave guide and the diameters of nuggets, the size of the nugget in the spot weld, i.e. the welding state can be readily detected.

The above-described waveforms can be clearly detected and displayed by setting the length L of the ultrasonic wave propagating path to a value in the range calculated from the aforementioned equation. If the length L is out of this range, the waveform in the case of welding thin plates each 1.4 mm or less in thickness cannot be detected and displayed clearly.

Figure 5:
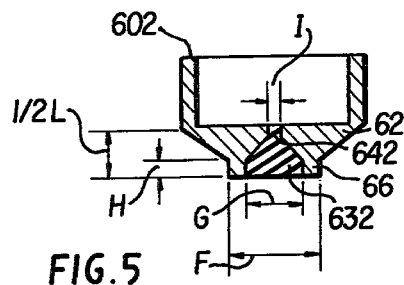
FIGS. 5, 6 and 7 are sectional views showing the wave guides in Examples 2, 3 and 4, respectively.

The construction of the wave guide may be such that, as shown in FIG. 5, it includes a conical structure converging towards the end portion of the ultrasonic wave porpagating section and a cylindrical structure, or a protruded annular structure 66 at the end portion. It goes without saying that the same effects as described above can be obtained with this wave guide. In addition, even if the contact surface 65 to be brought into contact with an inspection material is worn out or damaged from being used for a long time, the wave guide can be used again by machining the end portion of the protruded annular structure into a flat surface within the predetermined range of the ultrasonic wave propagating path length L.

Figure 6:
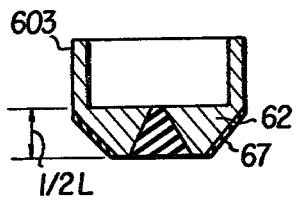

Furthermore, an external ultrasonic wave absorbing section may be provided by arranging the ultrasonic wave absorber on the outer wall of the cylindrical structure of the wave guide as shown in FIG. 6. In this case also, the same effects as described above can be obtained. In addition to this, irregular reflection in the cylindrical body serving as the ultrasonic wave propagating section can be effectively prevented. Therefore, detection and display can be achieved with higher accuracy. The materials of the ultrasonic wave absorber are the same as those of the above-described absorber.

Figure 7:
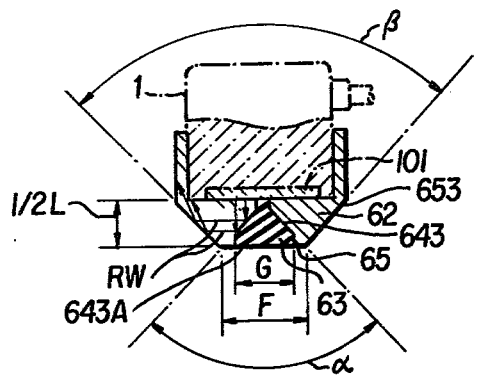

Another example of the wave guide is shown in FIG. 7. In this wave guide, the outer wall thereof is in the form of a cone which converges towards its end portion, and an inner hole formed in the wave guide, forming an internal ultrasonic wave absorbing section, is in the form of a cone which diverges towards the end portion. The conical angle $\alpha$ of the inside hole, which is formed by the opposite walls thereof, is in a range determined from the following equation (1), and the conical angle $\beta$ of the outer wall which is formed by the opposite outer walls thereof, is determined from the following equation (2).

The conical angle $\alpha$ of the inside hole $= 90 \pm 10$ degrees - - - (1)

The conical angle $\beta$ of the outer wall $\geq 180 - \alpha$ degrees - - - (2)

Using the above equations, the multiple reflection waves of the weld can be received and displayed more clearly.

This is because, where the wave guide according to the invention is constructed as shown in FIG. 7, when a transducer 101 produces a pulse or when a number of reflected wave pulses are produced as a result of the repetitive reflection in the ultrasonic wave propagating path of the wave guide, reflected waves RW having slight energy are produced. That is, the waves striking against the conical inside hole 643 of the wave guide, are reflected by the conical wall 643A of the conical inside hole 643. The reflected waves RW are propagated perpendicularly to the axis of the wave guide in FIG. 7 because the conical angle $\alpha$ of the inside hole is from 80 degrees to 100 degrees. As the conical angle $\beta$ of the outer wall of the wave guide is equal to or more than 80 degrees, the reflected waves RW are reflected and propagated in such a manner that they expand obliquely upwardly of the axis of the guide.

Accordingly, the wave reflected by the wall 643A of the conical inside hole of the guide cannot directly reach the transducer 101; that is, it is propagated toward the side wall of the guide through reflection and is damped. Therefore, even if the length L of the ultrasonic wave propagating path is further reduced within the above-described range, the multiple reflection waves of the weld are not interfered with by the reflected waves between the wall surfaces mentioned above, and therefore can be clearly received and displayed.

EXAMPLE 1

One example of this invention will be described with reference to FIGS. 2, 3, 4, 8 and 9, in which the inspection material was two sheets of steel plates which were spot-welded, and the weld of the inspection material was inspected with a device having a wave guide according to the invention.

Figure 2:
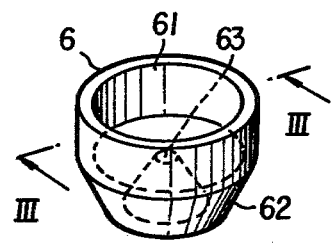
FIG. 2 is a perspective view showing a wave guide in Example 1.
Figure 3:
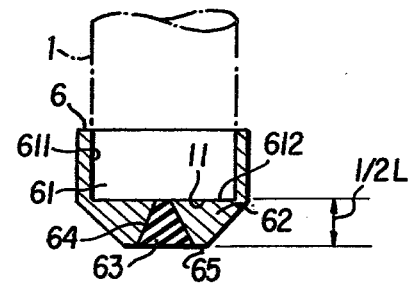
FIG. 3 is a vertical sectional view taken along line III—III in FIG. 2.

As shown in FIGS. 2 and 3, the wave guide 6 has a recess 61 defined on a conical cylinder 62. The recess 61 is adapted to receive the end portion of the probe. The conical cylinder 62 has a conical central hole 64 which diverges downwardly. The hole 64 is filled with an ultrasonic wave absorber 63 made of a mixture of paraffin and carbon powder. The conical cylinder 62 serves as an ultrasonic wave propagation portion. The filling of the ultrasonic wave absorber 63 was performed in accordance with the following method. First, a small quantity of the powder of the mixture was put into the hole 64 and was melted by heating, and then was cooled down. This process was repeatedly carried out, so that the absorber 63 was allowed to closely adhere to the wall of the hole 64. The distance in the axial direction between a probe connecting surface 612 of the wave guide which is brought into contact with the probe and an end surface 65 of the wave guide was 2.15 mm. Thus, the length L of the ultrasonic wave propagating path of the wave guide was 4.3 mm.

Figure 4:
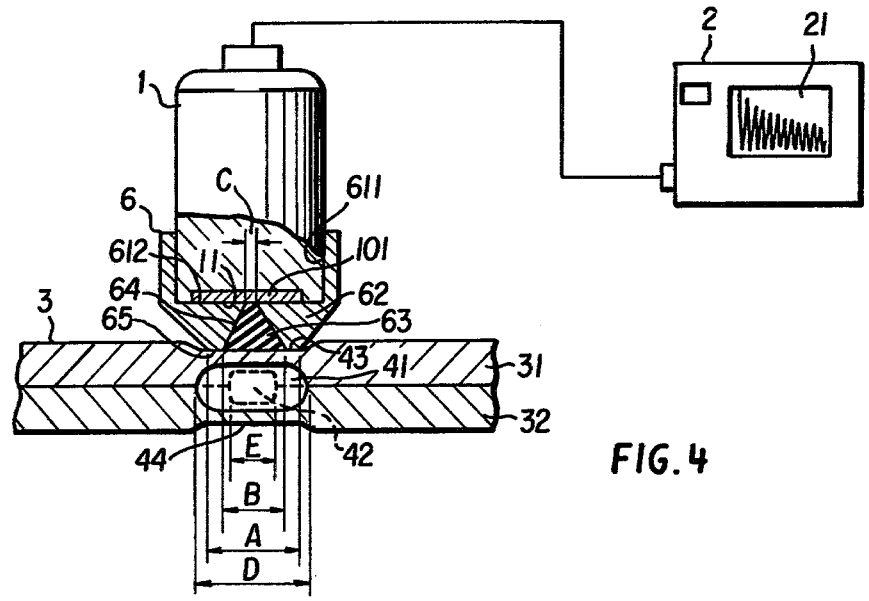
FIG. 4 is a sectional view showing a weld being inspected.

The wave guide 6 was fixedly secured to the probe 1 as shown in FIG. 4. In other words, the end portion of the probe 1 was inserted into the recess 61 of the wave guide 6 in such a manner that a small quantity of machine oil adapted as an ultrasonic wave coupling medium was interposed between the end surface 11 of the probe and the connecting surface 612 of the wave guide, and the side wall of the end portion of the probe was held by the inner wall 611 of the recess 61. The probe had a transducer 101 at its end.

The guide 6 was made of acrylic resin. The probe used was one which could output high resolution pulses at a frequency of 5 MHz. The outside diameter A and the inside diameter B of the conical cylinder 62 at the contact surface 65 thereof was 5.8 mm and 4.4 mm, respectively. The inside diameter C of the central hole 63 in the surface 612 brought into contact with the probe was 1 mm. The outside diameter of the end portion of the probe 1 was 13 mm. The inspection material 3 was obtained by spot-welding steel plates 31 and 32, each 1.4 mm in thickness, with an electrode tip 6 mm in diameter.

The ultrasonic wave propagating path length L was selected to be 4.3 mm due to the following reason. The aforementioned acrylic resin has an acoustic propagation speed of 2700 m/sec. Therefore, the wave length $\lambda$ is 0.54 mm $=(2700\times10^3(\text{mm/sec}))/(5\times10^6(1/\text{sec}))$. The above-described integer value n was eight (8). Therefore, the ultrasonic wave propagating path length L can be selected from a range of from $8\times0.54+0.2\times0.54=4.428$ mm) to $8\times0.54-0.2\times0.54=4.212$ mm. Therefore, in this example, the length L was selected to be 4.3 mm.

The inspection was made as follows: The contact surface 65 of the wave guide 6 fixedly secured to the probe 1 was brought through a small quantity of machine oil in contact with the surface 43 of an indent of the inspection material 3, which was caused by the welding. Under this condition, the ultrasonic wave was emitted by the probe 1 so that it was applied through the wave guide 6 into the inspection material 3. The reflection wave from the inspection material 3 was received by the probe 1 via the guide 6, so that a waveform was displayed on an oscilloscope 2 employed as a display unit shown in FIG. 1.

The measurement results were as follows:

(1-a) In the case where the weld of the inspection material 3 formed a nugget whose diameter D was equal to or larger than the outside diameter A of the contact surface 65 of the guide (for instance, the diameter D being 6.3 mm), the ultrasonic wave was applied in the form of a ring similar to the configuration of the contact surface 65 of the guide 6 into the plate 31 through the contact surface 65 and the surface 43. The incident ultrasonic wave was further advanced through the nugget 41 into the plate 32, and was then reflected by the surface 44 of the indented part of the plate 32. Most of the reflection wave, passing along the same path as that of the incident wave, was received by the probe 1. A part of the reflection wave was reflected by the surface 43 of the plate 31 again, and was therefore subjected to multiple reflection between the surfaces 43 and 44. This reflection wave was also received through the guide 6 by the probe 1.

In this inspection, the reflection wave received was displayed on the oscilloscope as shown in FIG. 8, in which the abscissa indicated time (microsecond) and the ordinate indicated reflected wave height on the oscilloscope (the same applies to FIG. 9).

In FIG. 8, a wave T was a transmission pulse emitted by the probe 1, and a wave $S_1$ was the first reflected wave from the contact surface 65 of the wave guide 1, i.e. the reflected wave which has made one round trip in the ultrasonic wave propagating path of the wave guide. In addition, waves $S_2$, $S_3$ and $S_4$ were the reflected waves which have made two, three and four round trips in the ultrasonic wave propagating path, respectively.

The reflected waves in the wave guide were absorbed by the wave guide itself and the ultrasonic wave absorber 63 filled in the central hole 64, and therefore they did not obstruct the display of multiple reflection wave 73 from the inspection material 3.

(1-b) In the case where the weld forms a nugget whose diameter E is smaller than the inside diameter B of the contact surface 65 of the guide 6 (for instance, the diameter E being 4.0 mm), the ultrasonic wave which entered the plate 31 was applied only outside the nugget 42, and therefore could not reach the plate 32. As a result, the multiple reflection was caused between the upper and lower surfaces of the plate 31. The received waves were as shown in FIG. 9. More specifically, the received wave included the multiple reflected wave 74 in the plate 31 in addition to the waves T, $S_1$, $S_2$, $S_3$ and $S_4$ similar to those in FIG. 8.

(1-c) In the case where the weld formed a nugget whose diameter was smaller than the outside diameter A of the contact surface 65 of the guide 6 but larger than the inside diameter B of the same (the diameter being for instance 5 mm), the received wave was a superposed reflection wave of the above-described multiple reflection waves 73 and 74, and was therefore rather intricate.

The multiple reflection wave 73 was different in pulse interval (second) from the multiple reflection wave 74. The pulse interval $t_1$ of the wave 73 obtained when a large nugget 41 showing a good weld was formed was approximately two times the pulse interval $t_2$ of the wave 74 obtained when a small nugget 42 showing a poor weld was formed. This interval $t_1$ was the pulse interval of the multiple reflection wave caused between the surface 43 of the plate 31 and the surface 44 of the plate 32. The interval $t_2$ was the pulse interval of the multiple reflection wave occurring between the surface 43 of the plate 31 and the surface of the plate 31 opposed to the plate 32.

As is apparent from the above description, according to this example of the invention, the reflected waves from the inspection material show distinctly different waveforms according to the size of nuggets in the welds. Therefore, the conditions of welds can be readily determined. Furthermore, when the pulse interval is short as in the pulse interval $t_2$, the weld can be determined to be unsatisfactory. Thus, the inspection can be performed readily, according to the invention.

The configuration of the central hole 64 of the wave guide 6 is such that it is conical and the diameter is made smaller on its side which is brought into contact with the probe 1, and therefore it is possible to effectively apply the high energy of the ultrasonic wave emitted by the probe 1 into the inspection material 3.

Furthermore, the ultrasonic wave propagating section 62 of the wave guide 6 is conically shaped with the outside diameter smaller on the side of its contact surface 65. Therefore, even a probe having an end surface larger than the diameter of the electrode tip can apply the ultrasonic wave into an inspection material readily.

As the probe 1 is fixedly secured to the guide 6 and only the guide is brought into contact with an inspection material, the end face of the probe is never damaged. In addition, as the probe is merely inserted into the guide, the guide can be readily replaced by a new one when damaged.

Furthermore, as the reflected waves in the guide can be absorbed by the ultrasonic wave absorber in the hole 64 of the guide, the display of the multiple reflection wave from the inspection material is never disturbed thereby. In the above description, the guide 6 is fixedly secured to the probe 1 by inserting the probe 1 in the recess 61 formed in the upper portion of the guide 6. However, they may be fixedly connected together by using screws or by utilizing an adhesive.

Comparison Example 1

A wave guide was fabricated which was similar in construction to the wave guide in Example 1 except that the ultrasonic wave propagating path length L was 4.7 mm. The weld of an inspection material was inspected under the same conditions as those in Example 1. The length L was selected from the range between the upper limit 4.428 mm obtained when the integer value n was 8 and the lower limit 4.752 mm obtained when the integer value n was 9. That is, not according to the equation $L = n\lambda + 0.2\lambda$.

Figure 12:
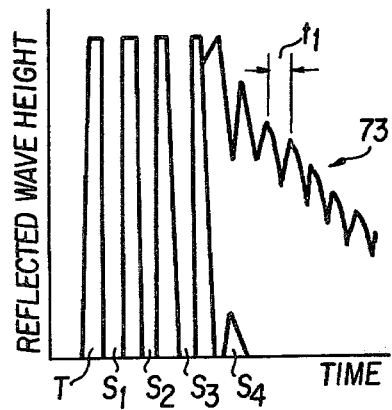
FIGS. 12 and 13 are waveform diagrams showing the relationship between reflected wave height and time in Comparison Example 1.
Figure 13:
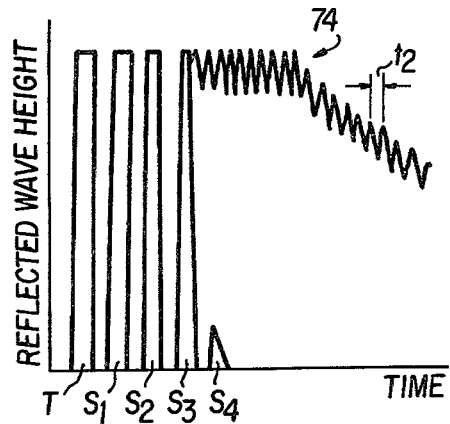

The measurement results are indicated in FIGS. 12 and 13 which are similar to FIGS. 8 and 9. FIG. 12 shows waveforms obtained when the weld is similar to that described in paragraph (1-a) of Example 1, and FIG. 13 shows waveforms obtained when the weld is similar to that described in paragraph (1-b) of Example 1.

As is apparent from FIGS. 12 and 13, in each waveform the multiple reflection waves received from the weld are strong enough, but the resolution of each of the multiple reflection waves is low.

In this case, the length L of the ultrasonic wave propagating path is not an integer multiple of the wave length $\lambda$. Therefore, after the first ultrasonic pulse emitted by the probe has entered the weld, the second, third and fourth reflected wave pulses which make round trips in the ultrasonic wave propagating path of the wave guide 1 are reflected and successively enter the weld. These many unnecessary incident waves cause multiple reflections in the weld, which are irregularly superposed on the multiple reflection of the first ultrasonic wave pulse in the weld. For this reason, the resolution of the multiple reflection is low.

This phenomenon becomes more significant as the thickness of the plates welded is decreased. In other words, as the individual pulse interval (time) of the multiple reflection wave is decreased, the pulse separation becomes worse.

On the other hand, the device employing the wave guide according to the invention can detect and display a clear waveform as shown in FIGS. 8 and 9. Thus, the performance of the device should be highly appreciated.

Comparison Example 2

Figure 17:
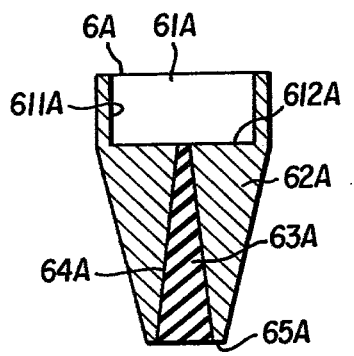
FIG. 17 is a sectional view showing a conventional wave guide described in Comparison Example 2.

Under the same conditions as those in Example 1, the weld was inspected with the conventional wave guide earlier developed by the inventors. This conventional wave guide, as shown in FIG. 17 and which has been already referred to, is relatively long, the distance between the annular end face 65A and the probe connecting surface 612 being 10 mm and the length of the ultrasonic wave propagating path therefore being 20 mm.

Figure 14:
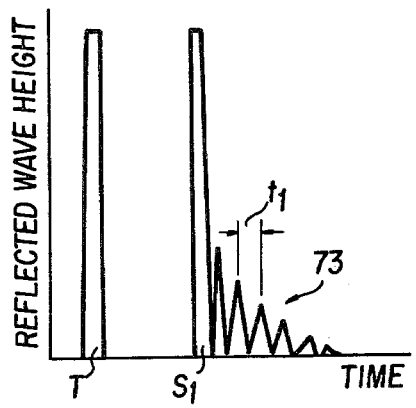
FIGS. 14 and 15 are waveform diagrams showing the relationship between reflected wave height and time in Comparison Example 2.
Figure 15:
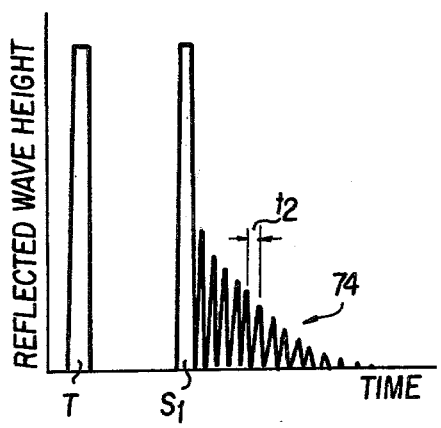

The measurement results are indicated in FIGS. 14 and 15 which are similar to FIGS. 8 and 9.

FIG. 14 is a waveform obtained when the weld was similar to that in paragraph (1-a) of Example 1, and FIG. 15 is a waveform obtained when the weld was similar to that in paragraph (1-b) of Example 1.

As is clear from FIGS. 14 and 15, in each waveform the multiple reflection wave received from the weld is very weak.

This is because the pulse strength of the probe emitting the high resolution pulse is originally weak, and as the conventional wave guide has a long propagating path, the necessary multiple reflection wave is also damped in this long propagating path. This phenomenon becomes more significant as the thickness of the plates welded is decreased. In other words, as the thickness of the weld is decreased, higher resolution pulses are required, and accordingly the strength of the multiple reflection wave received is further weakened.

Under conditions similar to those in Example 1, the weld was inspected with the conventional wave guide described above and a probe emitting an ordinary resolution pulse. In this case, the multiple reflections of the weld were superposed on one another and interfered with one another, and therefore it was impossible to inspect the weld.

On the other hand, in the device using the wave guide according to the invention, the multiple reflection waves received from the weld are strong, as shown in FIGS. 8 and 9. Therefore, a clear waveform could be detected and displayed. Thus, the device using the wave guide according to the invention was excellent in performance.

EXAMPLE 2

A wave guide 602 was fabricated which was similar in construction to that in Example 1 with the exception of the construction of its contact part which is brought into contact with an inspection material and the configuration of the central hole in the guide was as shown in FIG. 5. Similarly as in Example 1, a measurement was performed with this wave guide.

The section of the wave guide is shown in FIG. 5. As is apparent from FIG. 5, the aforementioned contact part is a protruded annular structure 66. More specifically, the protruded part of the structure 66 is in the form of a cylinder in which the inside diameter G and the outside diameter F are maintained unchanged over the height H. In FIG. 5, those parts which have been previously described with reference to FIG. 3, have therefore been similarly numbered. Reference numeral 62 designates an ultrasonic wave propagating section and reference numeral 642 designates a central hole which is filled with an ultrasonic wave absorber 632.

In this example, the inside diameter G of the contact part was 4.4 mm, the outside diameter F was 5.8 mm and the length L of the ultrasonic wave propagating path was 4.3 mm. The inside diameter I of the central hole 642 on the probe connecting side was 0.7 mm (similarly as in Example 1), and the height H of the protruded annular section 66 was 0.8 mm.

When measurement was performed with this wave guide in a manner similar to that in Example 1, an excellent waveform was detected and displayed similarly as in Example 1.

EXAMPLE 3

A wave guide 603 was fabricated which, as shown in FIG. 6, was similar to the wave guide in Example 1 except that an external ultrasonic wave absorbing section 67 was provided on the outer wall of a conical cylinder 62. Measurement was conducted with this wave guide and a high resolution pulse having a frequency of 10 MHz similar to that in Example 1 was used. The inspection material was obtained by spot-welding two steel plates 0.8 mm thick in a manner similar to that in Example 1.

The provision of the external ultrasonic wave absorbing section 67 was achieved in accordance with the following method. After an ultrasonic wave absorber, or a mixture of carbon powder and resin, was allowed to adhere to the outer wall and solidified, the thickness of the absorber was machined to approximately 0.5 mm.

Figure 10:
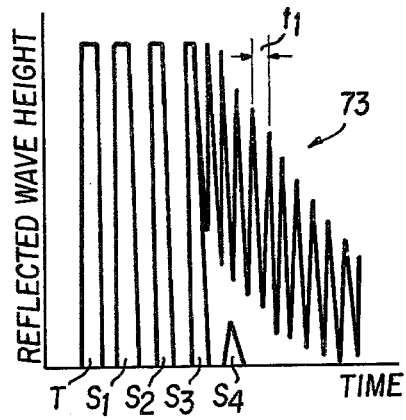
FIGS. 10 and 11 are waveform diagrams showing the relationship between reflected wave height and time in Example 3.
Figure 11:
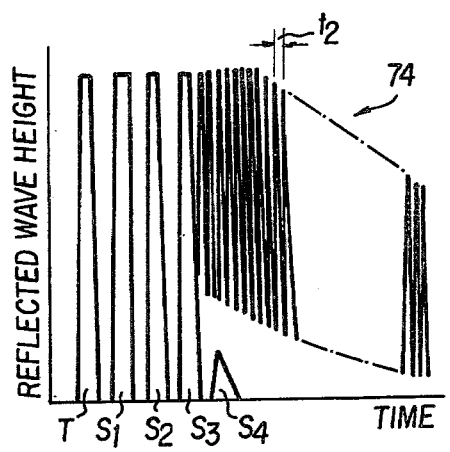

Measurement was carried out with this wave guide in a manner similar to that in Example 1. Although the inspection material was very thin, excellent detection and display could be obtained. The waveform obtained under the same conditions as those in paragraph (1-a) of Example 1 is shown in FIG. 10, and the waveform obtained under the same conditions as those in paragraph (1-b) is shown in FIG. 11, which are similar to FIGS. 8 and 9.

EXAMPLE 4

A wave guide 604 was fabricated which, as shown in FIG. 7, was similar to the wave guide in Example 1 except that the conical angle $\alpha$ of the conical central hole 643 which diverges downwardly was set to 90 degrees and the conical angle $\beta$ of the outer wall 653 was set to 90 degrees. Measurement was performed with this wave guide and a high resolution pulse having a frequency of 10 MHz, similar to that in Example 1 was used.

The wave length $\lambda$ of the ultrasonic wave was 0.27 mm. The length L of the ultrasonic wave propagating path was determined to be 3.8 mm from the following calculation:

$$L = 0.27 \text{ mm} \times 14 \pm 0.2 \text{ mm} \times 0.27 = 3.78 \text{ mm} \pm 0.054 \text{ mm}.$$

Thus, the distance between the contact surface 65 and the probe connecting surface 612 was 1.95 mm. The inside diameter G and the outside diameter F of the end face of the guide are 4.4 mm and 5.8 mm, respectively. A transducer 101, 6.35 mm in outside diameter, adapted to transmit and receive a high resolution ultrasonic pulse was provided on the end part of the probe 1 inserted into the guide 604.

Measurement was carried out for an inspection material obtained by spot-welding two steel plates 0.7 mm thick in a manner similar to that in Example 1. Although the inspection material was thinner, a multiple reflection wave which was clear and high in resolution could be displayed on the cathode-ray tube in the display unit 2 similar to that shown in FIGS. 10 and 11 with respect to Example 3.

It goes without saying that the aforementioned values $\alpha$ and $\beta$ can be applied to the wave guides used in Examples 1 through 3 within the above-described ranges.

Figure 16:
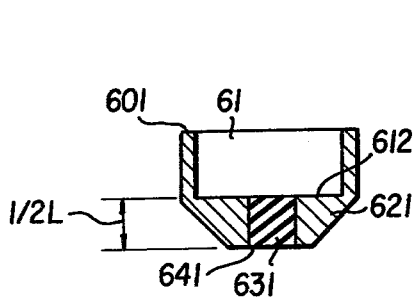
FIG. 16 is a sectional view showing a wave guide in another example of the invention.

Another example is shown in FIG. 16. The wave guide 601 can be obtained by modifying the wave guide 6 in Example 1. The conical central hole 64 of the guide 6 is changed into a cylindrical central hole 641, and an ultrasonic wave absorber 631 made of rubber is allowed to adhere to the inner wall of the cylindrical central hole 641 with an adhesive. The wave guide of this construction can be readily manufactured for the case where a probe emitting a strong ultrasonic wave is employed for inspection.

Obviously, numerous modifications and variations of the present invention are possible in light of the above teachings. It is therefore to be understood that within the scope of the appended claims, the invention may be practiced otherwise than as specifically described herein.

What is claimed as new and desired to be secured by Letters Patent of the United States is:

1. A device for inspecting spot welds, comprising:
    a probe for receiving a reflected wave from a material to be inspected;
    a weld state display unit for displaying a waveform, a pulse interval and a number of pulses of said reflected wave; and
    a wave guide connected to an end portion of said probe for guiding said reflected wave from said material to be inspected to said probe, said wave guide having an ultrasonic wave propagating section in the form of a cylinder and an internal ultrasonic wave absorbing section obtained by filling an inside hold of said cylinder with an ultrasonic wave absorbing material, said ultrasonic wave propagating section being so dimensioned that the length of an ultrasonic wave propagating path is within the range calculated from the equation:

$$L = n\lambda \pm 0.2\lambda$$

where n is an integer value, $\lambda$ is the wavelenght (mm) of an ultrasonic wave, and L is the length (mm) of said ultrasonic wave propagating path.

2. A device as claimed in claim 1, wherein said wave guide comprises a conical structure whose outer wall converges towards the end portion of said ultrasonic wave propagating section, and a protruded annular structure at said end portion.

3. A device as claimed in claim 1 wherein said wave guide has an external ultrasonic wave absorbing section obtained by arranging an ultrasonic wave absorbing material on the outer wall thereof.

4. A device according to claim 3, wherein said ultrasonic wave absorbing material of said external ultrasonic wave absorbing section is selected from the group consisting of rubber, paraffin, resin, and mixtures of at least one of said materials with tungsten powder or carbon powder.

5. A device as claimed in claim 1 wherein said wave guide is in the form of a cone whose outer wall converges towards the end thereof, and said inside hole of said internal ultrasonic wave absorbing section is in the form of a cone which diverges towards said end thereof, and that the conical angle $\alpha$ of said inside hole, which is formed by opposite walls thereof, is within the range of $90 \pm 10$ degrees and the conical angle $\beta$ of said outer wall of said wave guide, which is formed by opposite walls thereof, is equal to or larger than $180 - \alpha$ degrees.

6. A device according to claim 1, wherein the integer value n is selected in the range from 5 to 20.

7. A device according to claim 1, wherein said ultrasonic wave absorbing material is selected from the group consisting of rubber, paraffin, resin, and mixtures of at least one of said materials with tungsten powder or carbon powder.

* * * * *